United States Patent
Sgroi, Jr.

(10) Patent No.: US 11,147,561 B2
(45) Date of Patent: Oct. 19, 2021

(54) RELOAD ASSEMBLY FOR A CIRCULAR STAPLING DEVICE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 175 days.

(21) Appl. No.: 16/671,287

(22) Filed: Nov. 1, 2019

(65) Prior Publication Data

US 2020/0163675 A1 May 28, 2020

Related U.S. Application Data

(60) Provisional application No. 62/772,326, filed on Nov. 28, 2018.

(51) Int. Cl.
*A61B 17/3209* (2006.01)
*A61B 17/115* (2006.01)
*A61B 17/00* (2006.01)

(52) U.S. Cl.
CPC ...... *A61B 17/1155* (2013.01); *A61B 17/3209* (2013.01); *A61B 2017/00477* (2013.01)

(58) Field of Classification Search
CPC .................. A61B 17/1155; A61B 17/3209
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Apr. 20, 2020, issued in EP Appln. No. 19211851, 9 pages.

*Primary Examiner* — Nathaniel C Chukwurah

(57) ABSTRACT

A reload assembly a shell housing, a staple cartridge, a pusher assembly, a knife carrier, an annular knife, and a spring clip. The shell housing includes an inner housing portion that defines a central bore. The knife carrier includes a body defining a longitudinal axis and a cutout and is movable within the shell housing between advanced and retracted positions. The spring clip is supported on the inner housing portion of the shell housing and has a locking tang and an engagement portion. The spring clip is movable from a first position in which the locking tang is received within the cutout of the knife carrier to obstruct advancement of the knife carrier to a second position in which the locking tang is removed from the cutout of the knife carrier.

18 Claims, 10 Drawing Sheets

(56) References Cited

U.S. PATENT DOCUMENTS

| | | |
|---|---|---|
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant .................. A61B 17/115 227/179.1 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck |

(56) References Cited

U.S. PATENT DOCUMENTS

| | | |
|---|---|---|
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |

(56) References Cited

U.S. PATENT DOCUMENTS

| | | |
|---|---|---|
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |

(56) References Cited

U.S. PATENT DOCUMENTS

| | | |
|---|---|---|
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3165180 A2 | 5/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2016191907 A1 | 12/2016 |
| WO | 2017172582 A1 | 10/2017 |

* cited by examiner

RELOAD ASSEMBLY FOR A CIRCULAR STAPLING DEVICE

CROSS-REFERENCE TO RELATED APPLICATIONS

This application claims the benefit of and priority to U.S. Provisional Patent Application Ser. No. 62/772,326 filed Nov. 28, 2018, the entire disclosure of which is incorporated by reference herein.

BACKGROUND

1. Technical Description

The present disclosure is directed to circular stapling devices and, more particularly, to reload assemblies for circular stapling devices with structure to retain a knife carrier in a retracted position prior to attachment of an anvil assembly to the stapling device.

2. Background of Related Art

Conventional circular stapling devices include an elongate body and a shell or reload assembly supported on a distal portion of the elongate body. The reload assembly includes a shell housing, a staple cartridge supported on the shell housing having a plurality of staples, a pusher assembly, a knife defining a cylindrical cavity, and a knife carrier that supports the knife and is movable through the staple cartridge to core tissue. The pusher assembly includes an annular pusher and a staple pushing member that is engaged with the annular pusher and is movable to move the staple pushing member to eject staples from the staple cartridge.

After a stapling device has been operated to staple and cut tissue, the knife carrier and the knife are retracted to withdraw the knife into the shell housing and an anvil assembly is removed from the stapling device. This serves two purposes. The first purpose is that the knife is made accessible to a clinician to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife such that removal of the tissue donut from the cavity defined by the knife may cause advancement of the knife from within the shell housing to expose the cutting edge of the knife. This creates an unsafe condition for the clinician.

A continuing need exists in the art for a reload assembly that includes improved structure for retaining the knife carrier and knife in a retracted position when the anvil assembly is removed from the stapling device to minimize danger to the clinician

SUMMARY

One aspect of the present disclosure is directed to a reload assembly including a shell housing, a staple cartridge, a pusher, a knife carrier, an annular knife, and a spring clip. The shell housing includes an inner housing portion and an outer housing portion. The inner housing portion defines a central bore and is spaced from the outer housing portion to define an annular cavity between the inner and outer housing portions. The staple cartridge is supported on a distal portion of the shell housing and has a plurality of staple pockets. Each of the staple pockets receives a staple. The pusher is supported within the annular cavity and is movable between a retracted position and an advanced position to eject the staples from the staple cartridge. The knife carrier includes a body defining a longitudinal axis and a cutout and is movable within the annular cavity of the shell housing between advanced and retracted positions. The annular knife is supported on the knife carrier and has a distal portion defining a cutting edge. The spring clip is supported on the inner housing portion of the shell housing and has a locking tang and an engagement portion. The spring clip is movable from a first position in which the engagement portion extends across the central bore of the inner housing portion and the locking tang is received within the cutout of the knife carrier to obstruct advancement of the knife carrier to a second position in which the engagement portion is spaced from the central bore of the inner housing portion and the locking tang is removed from the cutout of the knife carrier.

Another aspect of the present disclosure is directed to a circular stapling device including an elongate body, an approximation mechanism, an anvil assembly, and a reload assembly. The elongate body has a proximal portion and a distal portion. The approximation mechanism is supported within the elongate body and includes a trocar. The anvil assembly includes an anvil shaft and an anvil head. The anvil shaft defines a bore that receives the trocar to releasably couple the anvil assembly to the trocar. The approximation mechanism is actuable to move the anvil assembly in relation to the staple cartridge between spaced and clamped positions. The reload assembly is supported on the distal portion of the elongate body and includes a shell housing, a staple cartridge, a pusher, a knife carrier, an annular knife, and a reload assembly. The shell housing includes an inner housing portion and an outer housing portion. The inner housing portion defines a central bore and is spaced from the outer housing portion to define an annular cavity between the inner and outer housing portions. The staple cartridge is supported on a distal portion of the shell housing and has a plurality of staple pockets. Each of the staple pockets receives a staple. The pusher is supported within the annular cavity of the shell housing and is movable between a retracted position and an advanced position to eject the staples from the staple cartridge. The knife carrier includes a body that defines a longitudinal axis and a cutout and is movable within the annular cavity of the shell housing between advanced and retracted positions. The annular knife is supported on the knife carrier and includes a distal portion defining a cutting edge. The spring clip is supported on the inner housing portion of the shell housing and has a locking tang and an engagement portion. The spring clip is movable from a first position in which the engagement portion extends across the central bore of the of the inner housing portion and the locking tang is received within the cutout of the knife carrier to obstruct advancement of the knife carrier to a second position in which the engagement portion is spaced from the central bore of the inner housing portion and the locking tang is removed from the cutout of the knife carrier.

In embodiments, the inner housing portion of the shell assembly includes a bushing and the spring clip is supported about the bushing.

In some embodiments, the bushing defines a recess that extends at least partially about the bushing and the spring clip is supported within the recess.

In certain embodiments, the bushing defines a slot that communicates the recess with the central bore of the inner housing portion and the engagement portion of the spring clip extends across the slot into the central bore when the spring clip is in the first position.

In embodiments, the bushing includes spaced flanges that define the recess and the locking tang of the spring clip extends radially outwardly of the spaced flanges when the spring clip is in the first position.

In some embodiments, the spaced flanges define flats positioned adjacent to the locking tang.

In certain embodiments, the pusher assembly includes an annular pusher and a pushing member that includes fingers that are received within the staple pockets of the staple cartridge.

In embodiments, the trocar is movable between the advanced and retracted positions through the central bore of the inner housing portion.

In some embodiments, the anvil shaft is positioned to engage the engagement portion of the spring clip to move the spring clip from its first position to its second position when the anvil assembly is moved towards the clamped position.

In certain embodiments, the stapling device includes a handle assembly and the elongate body is supported on the handle assembly.

In embodiments, the elongate body is adapted to be coupled to a robotic surgical system.

In embodiments, the trocar is positioned and configured to engage the engagement portion of the spring clip to move the spring clip from its first position to its second position when the anvil assembly is moved towards the clamped position.

BRIEF DESCRIPTION OF THE DRAWINGS

Various embodiments of the presently disclosed reload assembly are described herein below with reference to the drawings, wherein.

DETAILED DESCRIPTION OF EMBODIMENTS

Figure 1:
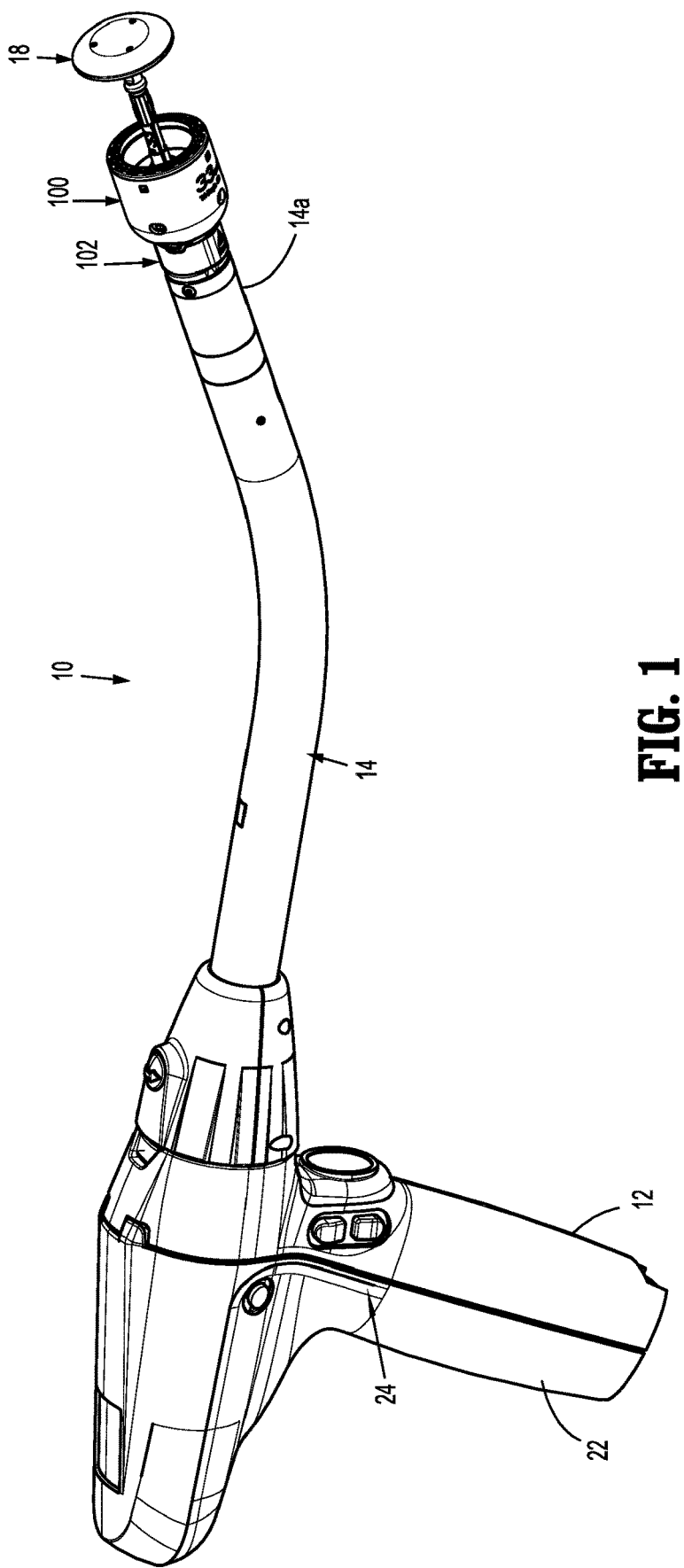
FIG. 1 is a side perspective view of a circular stapling device including an exemplary embodiment of the presently disclosed reload assembly in accordance with the present disclosure.

The presently disclosed reload assembly will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
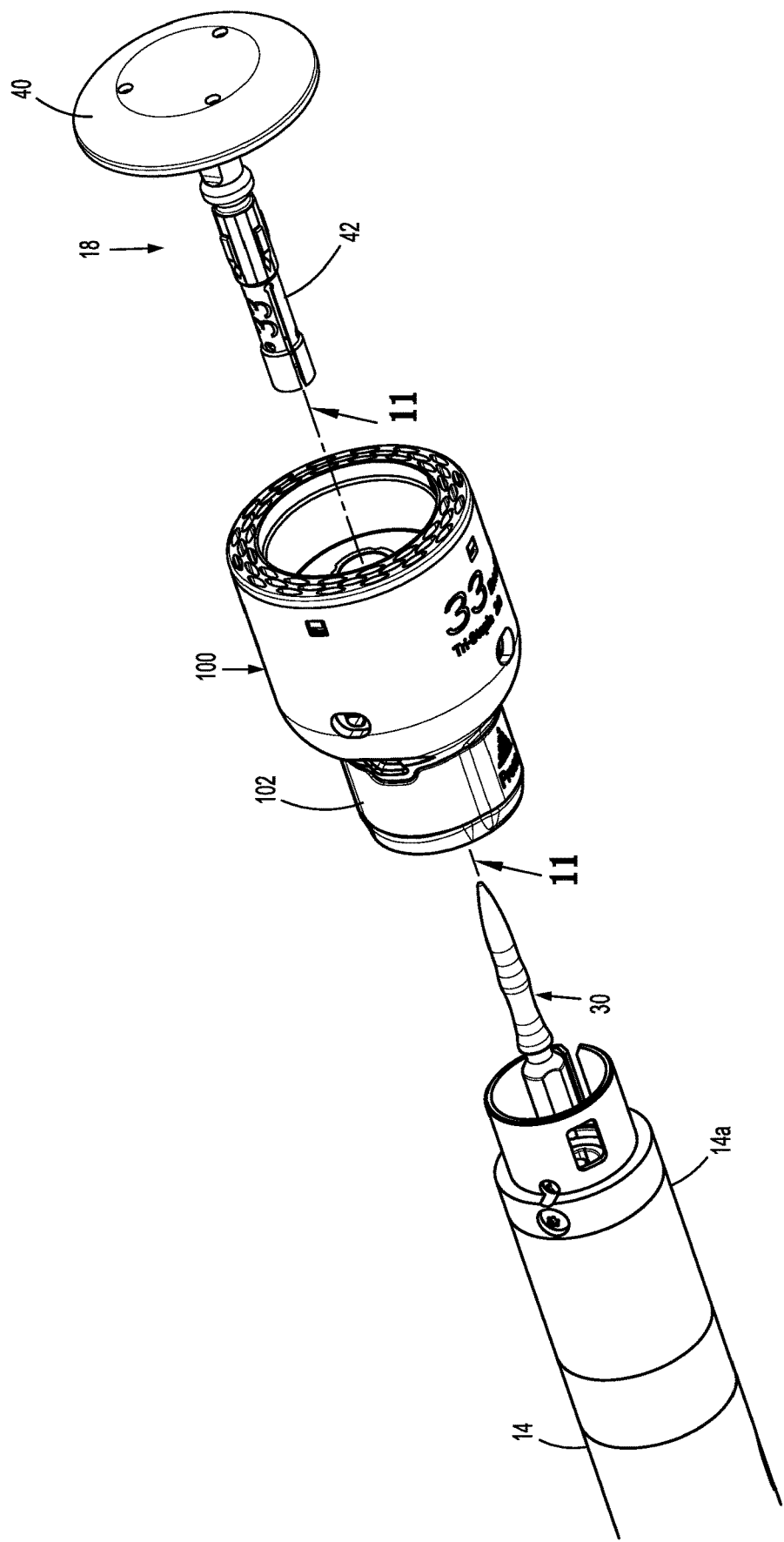
FIG. 2 is a side perspective exploded view of a distal portion of the circular stapling device of FIG. 1 including the reload assembly, an anvil assembly, and a distal portion of an elongate body of the surgical stapling device.

FIGS. 1 and 2 illustrate a circular stapling device 10 including an exemplary embodiment of the presently disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as described below. The reload assembly 100 includes a proximal portion 102 (FIG. 1) that is releasably coupled to a distal portion 14a of the elongate body 14. The handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12. The elongate body 14 is in the form of an adaptor assembly that translates power from the handle assembly 12 to the reload and anvil assemblies 100, 18, respectively. Examples of electrically powered stapling devices can be found in U.S. Pat. No. 9,055,943 (the '943 patent), U.S. Pat. No. 9,023,014 (the '014 patent), and U.S. Publication Nos. 2018/0125495, and 2017/0340351 which are incorporated herein by reference in their entirety. Alternately, it is envisioned that the present disclosure could also be incorporated into a manually powered stapling device such as disclosed in U.S. Pat. No. 7,303,106 (the '106 patent) or a stapling device that is configured for use with a robotic system such as disclosed in U.S. Pat. No. 9,962,159 (the '159 patent) that does not include a handle assembly. The '106 and '159 patents are also incorporated herein by reference in their entirety.

Figure 12:
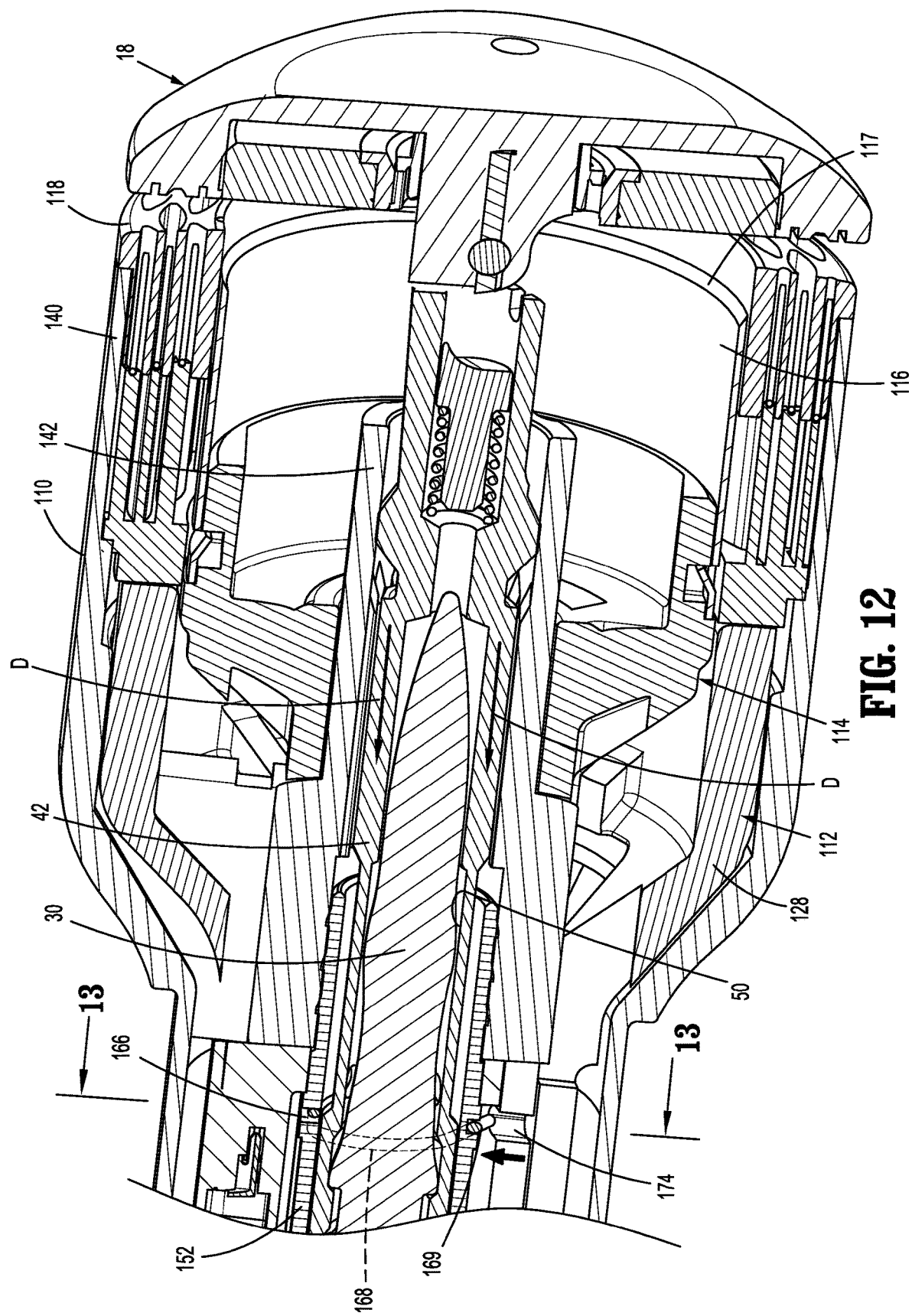
FIG. 12 is a cross-sectional view taken along section line 11-11 of FIG. 2 with the reload assembly secured to the adaptor assembly of the surgical stapling device, the anvil assembly attached to the trocar assembly, and the anvil assembly in a clamped position in relation to the reload assembly.

Referring to FIG. 2, the adaptor assembly 14 includes a trocar 30 that extends from the distal portion 14a of the adaptor assembly 14 and through the reload assembly 10. The trocar 30 forms part of an approximation mechanism (not shown) of the stapling device 10. The anvil assembly 18 includes an anvil head 40 and an anvil shaft 42. The anvil shaft 42 is configured to be releasably coupled to the trocar 30 to support the anvil assembly 18 on the distal portion 14a of the adaptor assembly 14. The trocar 18 of the approximation mechanism is movable in relation to the reload assembly 100 to move the anvil assembly 18 in relation to the reload assembly 100 between a spaced position (FIG. 1) and a clamped position (FIG. 12). For a more detailed description of the trocar 30, the anvil assembly 18, and the approximation assembly (not shown) of the stapling device 10, see the '106.

Figure 3:
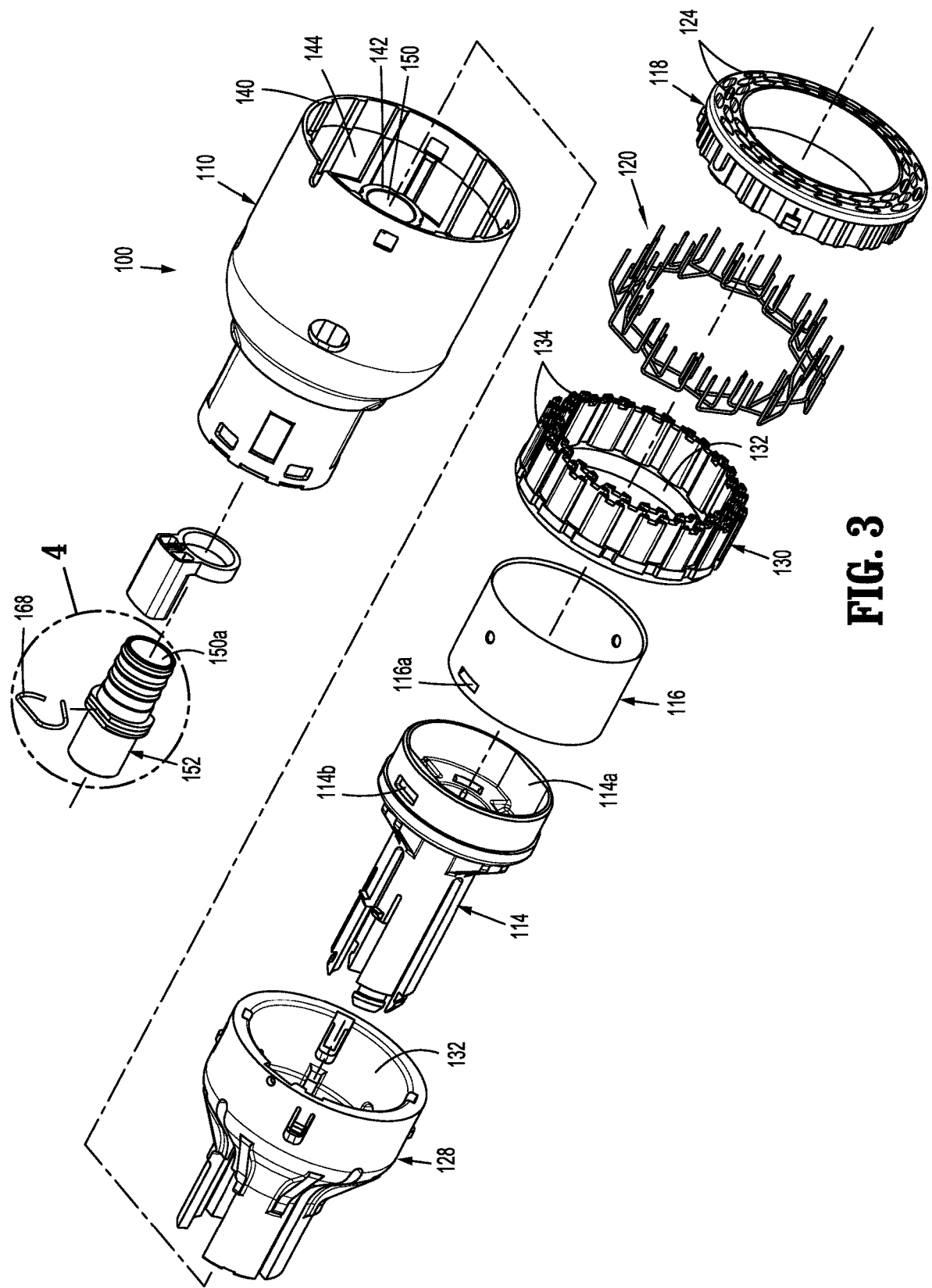
FIG. 3 is an exploded side perspective view of the reload assembly of FIG. 2.
Figure 4:
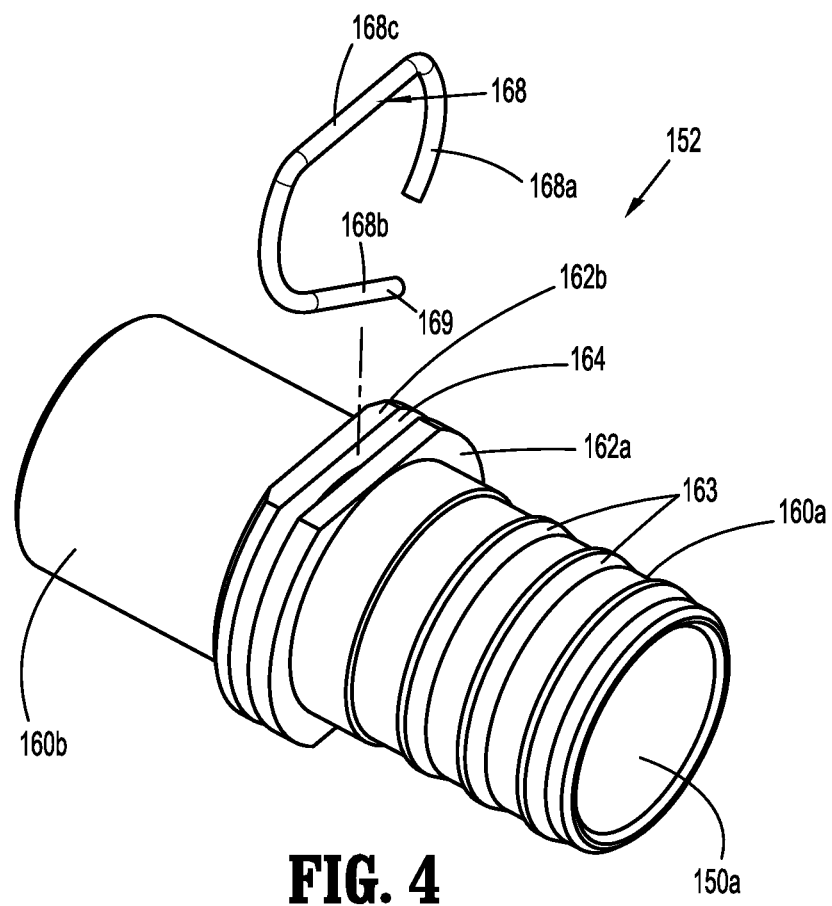
FIG. 4 is an enlarged view of the indicated area of detail shown in FIG. 3.
Figure 5:
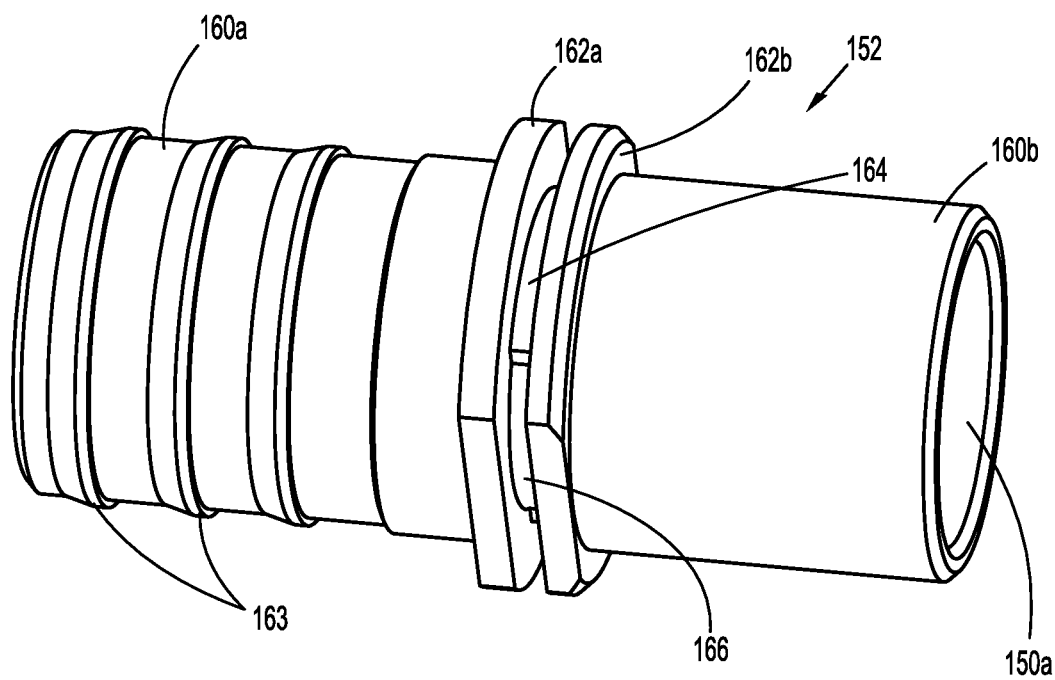
FIG. 5 is a side perspective view of a bushing of the reload assembly shown in FIG. 3.
Figure 6:
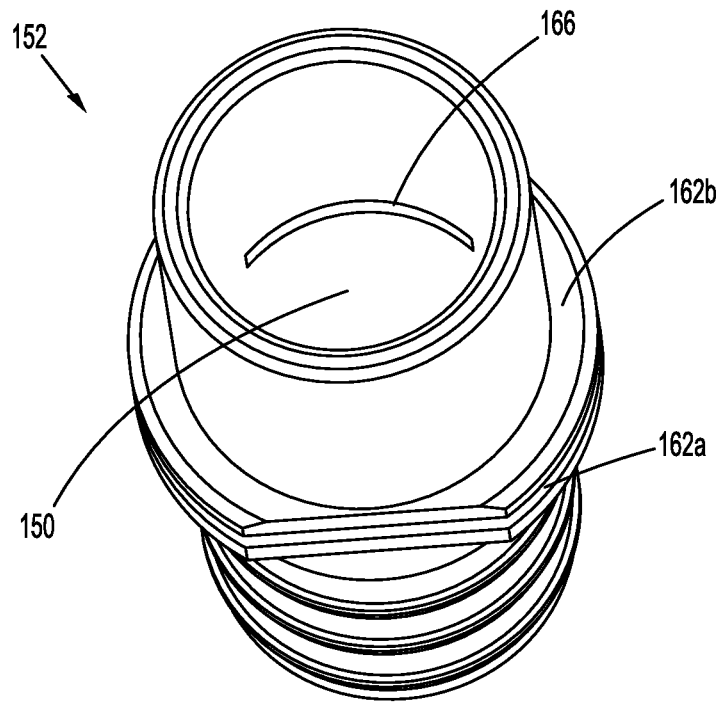
FIG. 6 is a perspective view from the proximal end of the bushing shown in FIG. 6.
Figure 7:
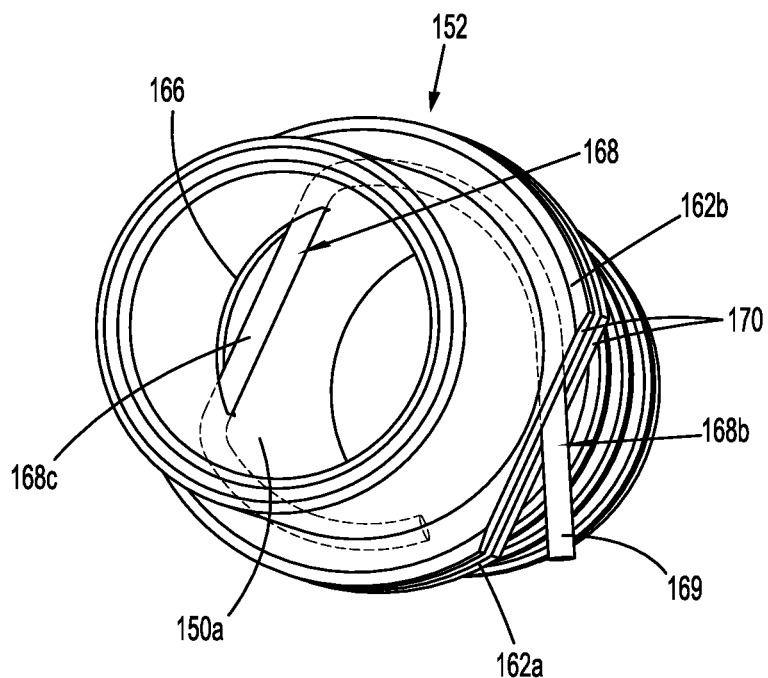
FIG. 7 is a perspective view from the proximal end of the bushing shown in FIG. 6 rotated ninety degrees.
Figure 8:
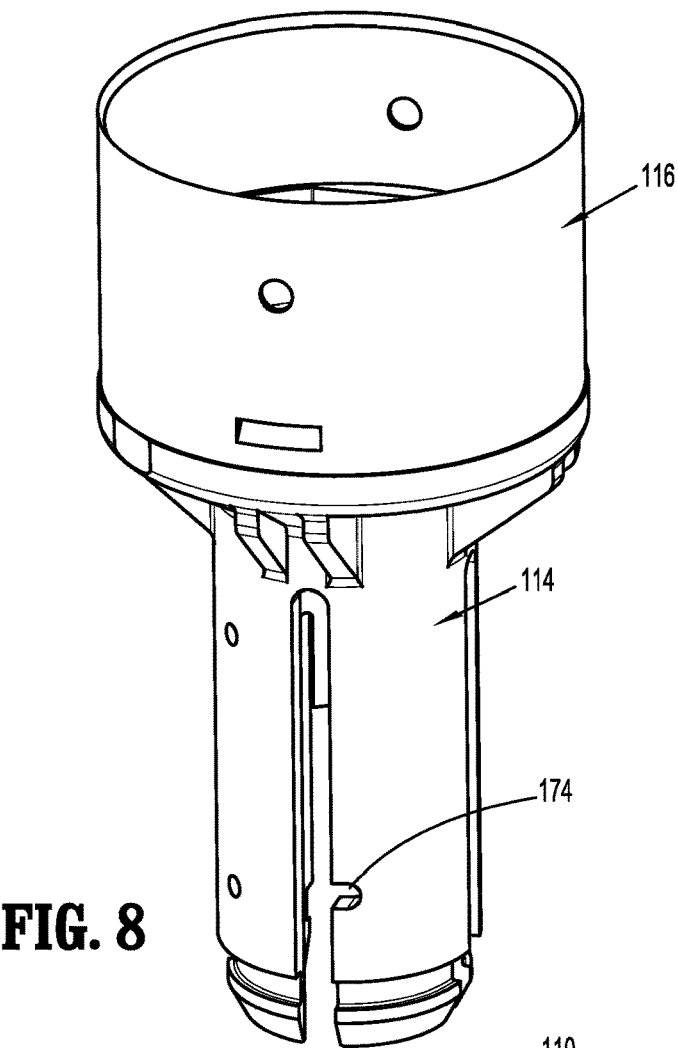
FIG. 8 is a side perspective view of a knife carrier of the reload assembly shown in FIG. 3.
Figure 9:
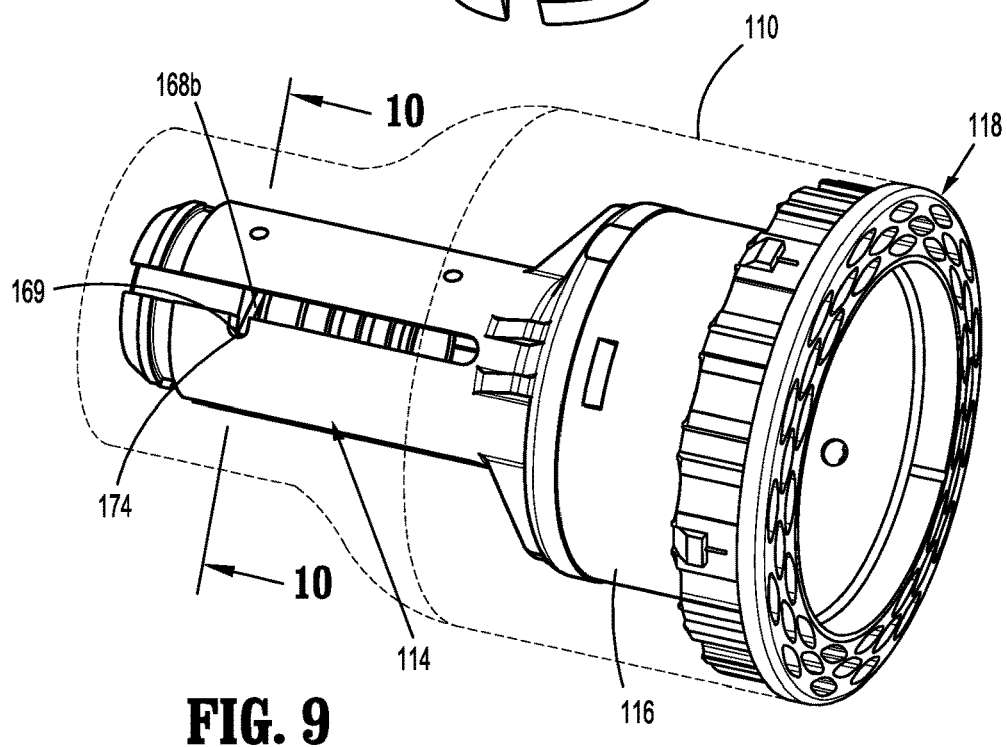
FIG. 9 is a side perspective view of the knife carrier and the shell housing of the reload assembly shown in FIG. 3 with the knife carrier in a retracted position within the shell housing and the shell housing shown in phantom.

Referring to FIG. 3, the reload assembly 100 includes a shell housing 110, a pusher assembly 112 (FIG. 11), a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one of the plurality of staples 120. The pusher assembly 112 includes an annular pusher 128 and a staple pushing member 130 that together define a longitudinal through bore 132. The pusher 128 has a distal portion that abuts a proximal portion of the staple pushing member 130 such that distal movement of the pusher 128 within the shell housing 110 causes distal movement of the staple pushing member 130. The staple pushing member 130 of the reload 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 130 is moved distally within the shell housing 110 from a retracted position to an advanced position.

The shell housing 110 includes an outer housing portion 140 and an inner housing portion 142 that are spaced from each other to define an annular cavity 144. The pusher assembly 112 (FIG. 11), the knife carrier 114, and the annular knife 116 are movable within the annular cavity 144 of the shell housing 110 between the retracted and advanced positions. The pusher assembly 112 is movable from its retracted position to its advanced position independently of the knife carrier 114 and the annular knife 116 to eject the staples 120 from the staple cartridge 118. The annular knife 116 is supported within a cylindrical cavity 114a defined by the knife carrier 114. In embodiments, the knife 116 includes protrusions 116a that are received in recesses 114b defined in the knife carrier 114 to secure the knife 116 within the cylindrical cavity 114a of the knife carrier 114. Alternately, other fastening techniques may be used to secure the knife 116 to the knife carrier 114. After the pusher assembly 112 (FIG. 11) is moved from its retracted position to its advanced position, the knife carrier 114 can be moved from its retracted position to its advanced position to cut tissue positioned radially inward of the staple cartridge 118.

The inner housing portion 142 of the shell housing 110 defines a through bore 150 that receives the anvil shaft 42 of an anvil assembly 18 (FIG. 2) and the trocar 30 of the adaptor assembly 14. The through bore 150 also supports a bushing 152 that defines a through bore 150a that is coaxial with the through bore 150 of the inner housing portion 142 of the shell housing 110. In embodiments, the bushing 152 is formed of a high strength material, e.g., metal, to provide added strength to the inner housing portion 142 of the shell housing 110.

The reload assembly 100 may include an e-prom 154 that is supported on the shell housing 110. As is known in the art, the e-prom 154 communicates with the adaptor assembly 14 to provide information to the adaptor assembly 14 and handle assembly 12 related to characteristics of the reload assembly 10.

Referring to FIGS. 4-7, the bushing 152 includes a distal portion 160a and a proximal portion 160b that are separated by spaced flanges 162a and 162b. The spaced flanges 162a and 162b define a recess 164 that extends at least partially about the bushing 152. The bushing 152 includes a slot 166 that extends through the bushing 152 and connects the recess 164 to the through bore 150a. In embodiments, the distal portion 160a of the bushing 152 includes a series of spaced annular ribs or protrusions 163 that are received within the inner housing portion 142 of the shell housing 110 to frictionally secure the bushing 152 within the inner housing portion 110 of the shell housing 110. It is envisioned that other fastening techniques including crimping, welding, over molding, or the like may be used to secure the bushing 152 within the shell housing 110.

The bushing 152 supports a resilient spring clip 168. More specifically, the spring clip 168 is supported within the recess 164 defined between the flanges 162a and 162b of the bushing 152. In embodiments, the spring clip 168 has a substantially C-shaped configuration that can be deformed to be positioned about the bushing 152 within the recess 164. In embodiments, the spring clip 168 has a first end 168a, a second end 168b defining a locking tang 169, and a central or engagement portion 168c. The central portion 168c of the spring clip 168 is extends across the slot 166 and into the through bore 150 defined by the bushing 152 (FIG. 7) when the spring clip 168 is received within the recess 164. The second end 168b of the spring clip 168 is angled outwardly of the bushing 152 such that the locking tang 169 extends from the recess 164 defined by the flanges 162a and 162b. In embodiments, the flanges 162a and 162b of the bushing 152 include flats 170 (FIG. 7) that are aligned with the locking tang 169 of the spring clip 168 such that the locking tang 169 extends from the recess 164. The flats 170 should be aligned with the slot 166 to allow the second end 168b of the spring clip 168 to extend from the recess 164. In embodiments, the spring clip 168 can be formed from a variety of resilient materials including spring steel, polymers, etc.

It is envisioned that the bushing 152 may be integrally or monolithically formed with the inner housing portion 142 of the shell housing 110 and/or that the spring clip may be supported on the inner housing portion 142 of the shell housing 110.

Figure 10:
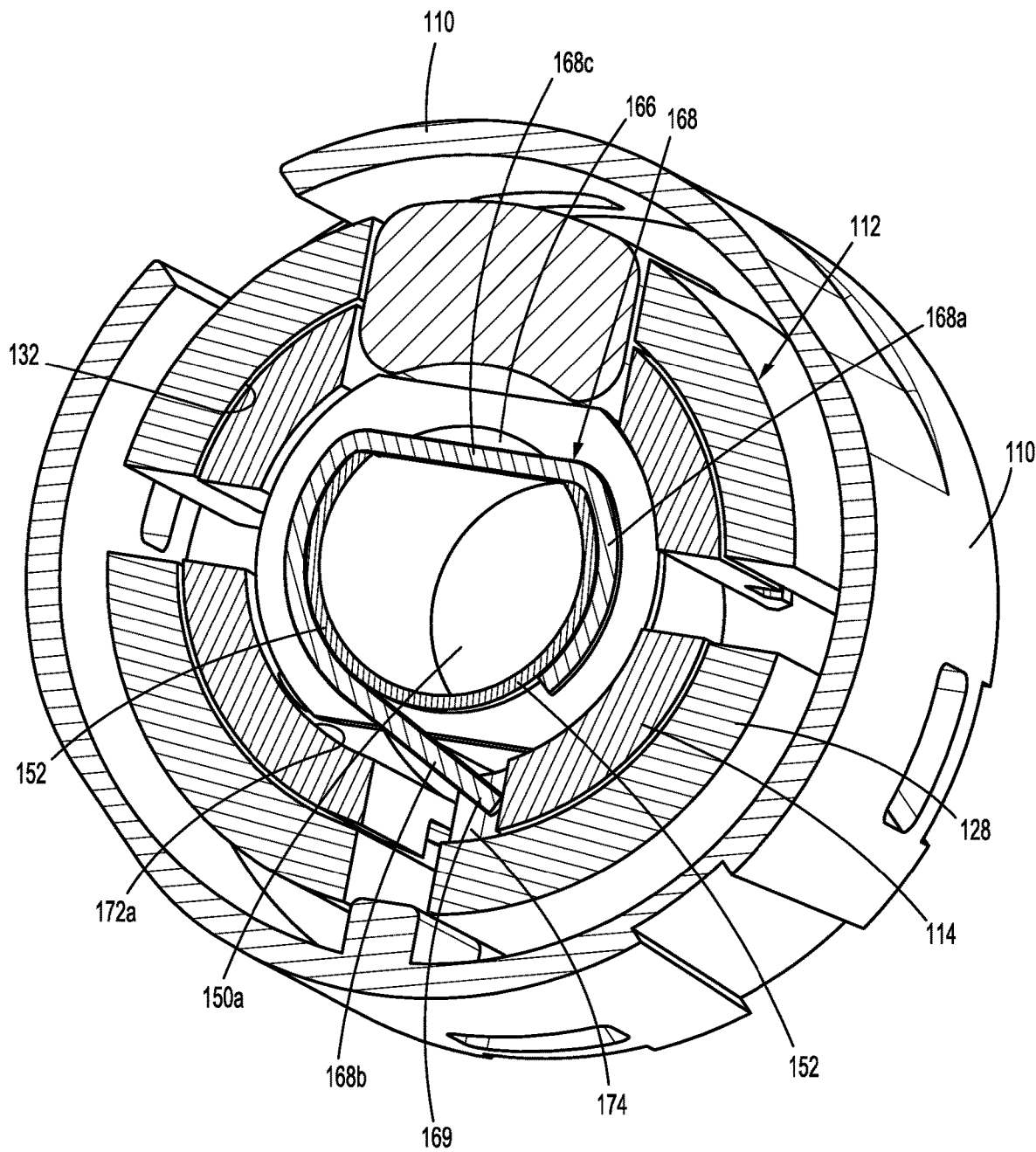
FIG. 10 is a cross-sectional view taken along section line 10-10 of FIG. 9.
Figure 11:
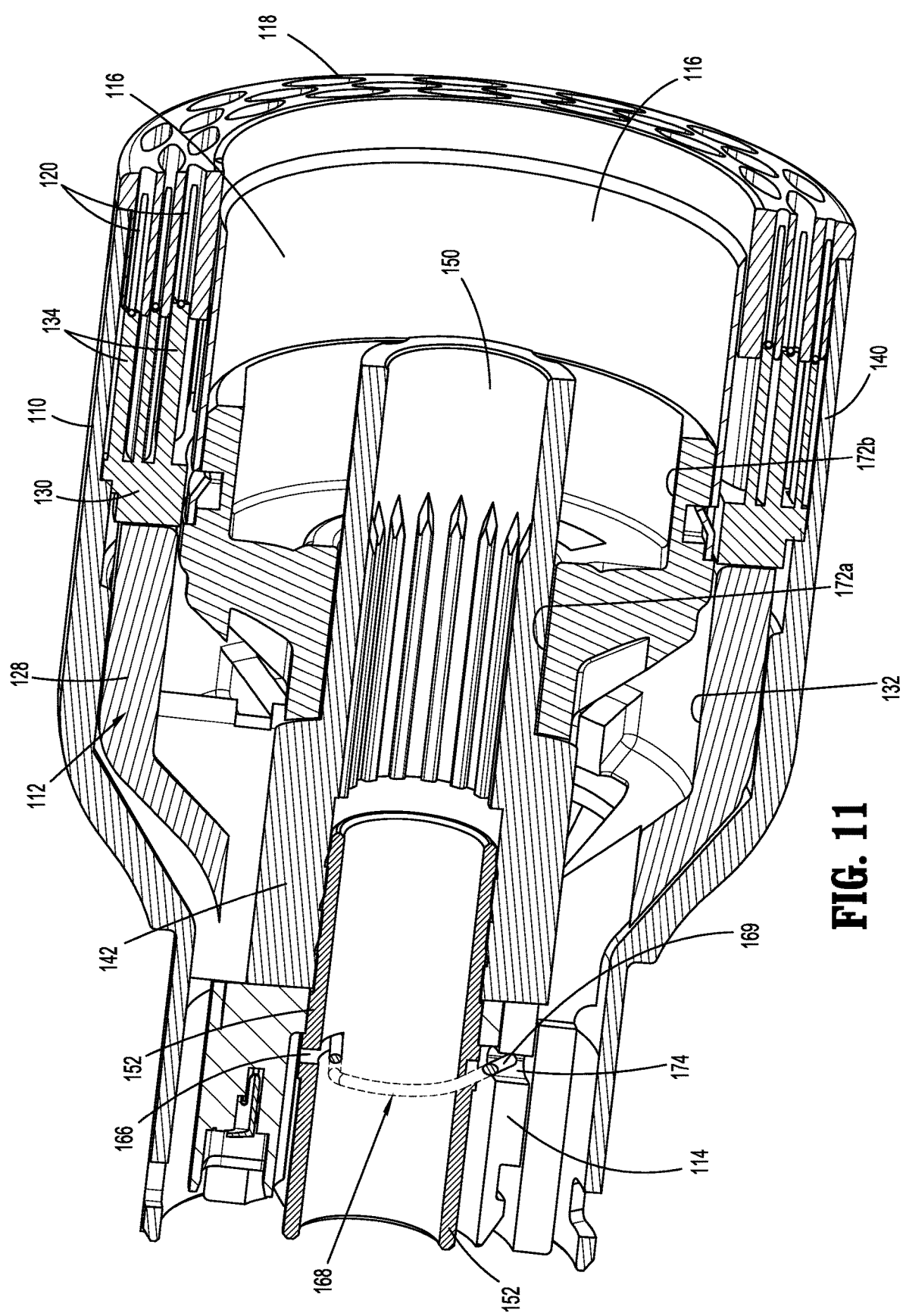
FIG. 11 is a cross-sectional view taken along section line 11-11 of FIG. 2.

Referring to FIGS. 8-11, the knife carrier 114 is movably positioned within the through bore 132 (FIG. 11) of the pushing assembly 112 between its retracted and advanced positions and defines a stepped central bore 172. The stepped central bore 172 includes a small diameter proximal portion 172a and a larger diameter distal portion 172b (FIG. 11). The proximal portion 172a of the central bore 172 of the knife carrier 114 receives the inner housing portion 142 and the bushing 152 (FIG. 11) of the shell housing 110 such that the knife carrier 114 slides about the inner housing portion 142 and the bushing 152 between retracted and advanced positions.

The proximal portion 172a of the knife carrier 114 defines a cutout 174. When the knife carrier 114, and thus the knife 116, are in their retracted positions (FIGS. 10 and 11), prior to attachment of an anvil assembly 18 to the trocar 30, the cutout 174 is aligned with locking tang 169 at the second end 168b of the spring clip 168 such that the locking tang 169 is received within the cutout 174. When the locking tang 169 of the spring clip 168 is positioned within the cutout 174, the spring clip 168 obstructs advancement of the knife carrier 114 and the knife 116 about the inner housing portion 142 of the shell housing 110. As can be seen in FIG. 10, prior to attachment of the anvil assembly 18 to the trocar 30, the central portion 168c of the spring clip 168 extends across the through bore 150a of the bushing 152.

Prior to attachment of the reload assembly 100 to the adaptor 14, the locking tang 169 is aligned with and received within the cutout 174 of the knife carrier 114 to lock the knife carrier 114 in its retracted position. This minimizes the risk of injury to a clinician during transport of the reload assembly 100 prior to use.

Figure 13:
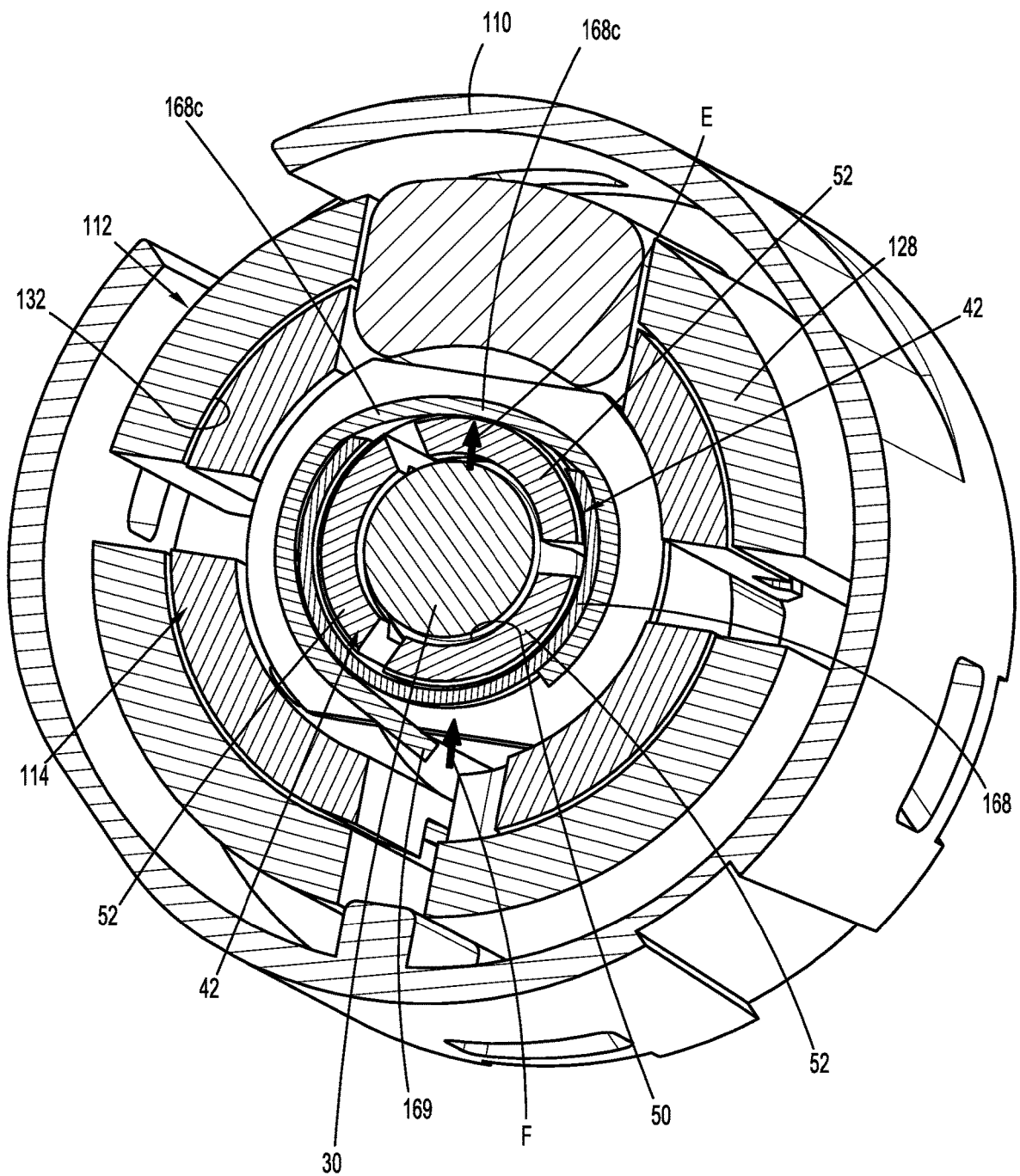
FIG. 13 is a cross-sectional view taken along section line 13-13 of FIG. 12.

Referring to FIGS. 12 and 13, when an anvil assembly 18 is attached to the trocar 30, the trocar 30 is received within a bore 50 defined by flexible legs 52 of the anvil shaft 42 such that the anvil shaft 42 is aligned with the central bore 150 of the inner housing portion 142 and the central bore 150a of the bushing 152. When the anvil assembly 18 and the reload assembly 100 are in the spaced position (FIG. 1), the proximal end of the legs 52 of the anvil shaft 42 are spaced distally of the central portion 168c of the spring clip 168 such that the spring clip 168 remains within the through bore 150a of the bushing 152. In this position, the locking tang 169 of the spring clip 168 remains aligned with and received within the cutout 174 of the knife carrier 114 to lock the knife carrier 114 in its retracted position.

When the anvil assembly 18 and the reload assembly 100 are retracted to the clamped position in the direction indicated by arrow "D" in FIG. 12, the trocar 30 and the anvil shaft 42 of the anvil assembly 18 are drawn into the inner housing portion 142 of the shell housing 110 and into the bushing 152. As the anvil assembly 18 and the reload assembly approach the clamped position, the proximal end of the legs 52 of the anvil shaft 42 engage the central portion 168c of the spring clip 168 and deform the spring clip 168 in the direction indicated by arrow "E" in FIG. 13. As the central portion 168c moves in the direction indicated by arrow "E", the locking tang 169 on the second end 168b of the spring clip 168 is pulled from the cutout 174 in the knife carrier 114 in the direction indicated by arrow "F" to release the knife carrier 114 for advancement. The stapling device 10 can be actuated to fire staples 120 (FIG. 3) and cut tissue.

After the stapling device is fired and the knife carrier 114 is retracted, the second end 168b of the spring clip 168 moves back into alignment with the cutout 174 in the knife carrier 114. When the anvil assembly 18 and the reload assembly 100 are returned to their spaced position, the legs 52 of the anvil shaft 42 move out of engagement with the central portion 168c of the spring clip 168 to allow the central portion 168c of the spring clip snap into the central bore 150a of the bushing 152 and to allow the locking tang 169 on the second end of the spring clip 168 to move back into the cutout 174 of the knife carrier 114 to once again obstruct advancement of the knife carrier 114.

The presently disclosed reload assembly 100 prevents advancement of the knife carrier 114 in a first condition in which the anvil assembly 18 is not attached to the trocar 30 of the stapling device 10 and in a second condition in which the anvil assembly 18 is attached to the trocar 30 but is in a spaced position in relation to the staple cartridge 118. In both these conditions, the cutting edge 117 of the knife 116 may be accessible by the clinician if the knife is advanced. Preventing advancement of the knife carrier 114 and knife 116 in these conditions minimizes any likelihood that the clinician will be injured by an exposed cutting edge 117 of the knife 116 during disengagement of the reload assembly 100 from the adaptor assembly 14 during removal of a tissue donut from the cavity defined by the annular knife 116.

In alternate embodiments, the trocar 30 (FIG. 12) may be configured to engage the central portion 168c of the spring clip 168 to unlock the knife carrier 114 as the trocar 30 is moved between its retracted and advanced positions. For example, the trocar 30 may be configured to engage the central portion 168c of the spring clip 168 before the anvil shaft 42 of the anvil assembly 18 engages the central portion 168c. In such an embodiment, the locking tang 169 of the spring clip 168 would be removed from the cutout 174 in the knife carrier 114 before the proximal end of the legs 52 of the anvil shaft 42 engage the central portion 168c of the spring clip 168.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A reload assembly comprising:
   a shell housing including an inner housing portion and an outer housing portion, the inner housing portion defining a central bore and being spaced from the outer housing portion to define an annular cavity between the inner and outer housing portions;
   a staple cartridge supported on a distal portion of the shell housing, the staple cartridge having a plurality of staple pockets, each of the staple pockets receiving a staple;
   a pusher supported within the annular cavity, the pusher movable between a retracted position and an advanced position to eject the staples from the staple cartridge;
   a knife carrier including a body defining a longitudinal axis and a cutout, the knife carrier movable within the annular cavity of the shell housing between advanced and retracted positions;
   an annular knife supported on the knife carrier, the annular knife having a distal portion defining a cutting edge; and
   a spring clip supported on the inner housing portion of the shell housing, the spring clip having a locking tang and an engagement portion, wherein the spring clip is movable from a first position in which the engagement portion extends across the central bore of the of the inner housing portion of the shell housing and the locking tang is received within the cutout of the knife carrier to obstruct advancement of the knife carrier to a second position in which the engagement portion is spaced from the central bore of the inner housing portion of the shell housing and the locking tang is removed from the cutout of the knife carrier.

2. The reload assembly of claim 1, wherein the inner housing portion of the shell assembly includes a bushing and the spring clip is supported about the bushing.

3. The reload assembly of claim 2, wherein the bushing defines a recess that extends at least partially about the bushing and the spring clip is supported within the recess.

4. The reload assembly of claim 3, wherein the bushing defines a slot that communicates the recess with the central bore of the inner housing portion of the shell housing, the engagement portion of the spring clip extending across the slot into the central bore when the spring clip is in the first position.

5. The reload assembly of claim 3, wherein the bushing includes spaced flanges that define the recess, the locking tang of the spring clip extending radially outwardly of the flanges when the spring clip is in the first position.

6. The reload assembly of claim 5, wherein the spaced flanges define flats positioned adjacent the locking tang.

7. The reload assembly of claim 1, wherein the pusher includes an annular pusher and a pushing member, the pushing member including fingers that are received within the staple pockets of the staple cartridge.

8. A circular stapling device comprising;
an elongate body having a proximal portion and a distal portion;
an approximation mechanism supported within the elongate body, the approximation mechanism including a trocar;
an anvil assembly including an anvil shaft and an anvil head, the anvil shaft defining a bore that receives the trocar to releasably couple the anvil assembly to the trocar, wherein the approximation mechanism is actuable to move the anvil assembly in relation to the staple cartridge between spaced and clamped positions;
a reload assembly supported on the distal portion of the elongate body, the reload assembly including:
a shell housing including an inner housing portion and an outer housing portion, the inner housing portion defining a central bore and being spaced from the outer housing portion to define an annular cavity between the inner housing portion and the outer housing portion;
a staple cartridge supported on a distal portion of the shell housing, the staple cartridge having a plurality of staple pockets, each of the staple pockets receiving a staple;
a pusher supported within the annular cavity of the shell housing, the pusher movable between a retracted position and an advanced position to eject the staples from the staple cartridge;
a knife carrier including a body defining a longitudinal axis and a cutout, the knife carrier movable within the annular cavity of the shell housing between advanced and retracted positions;
an annular knife supported on the knife carrier, the annular knife having a distal portion defining a cutting edge; and
a spring clip supported on the inner housing portion of the shell housing, the spring clip having a locking tang and an engagement portion, wherein the spring clip is movable from a first position in which the engagement portion extends across the central bore of the inner housing portion of the shell housing and the locking tang is received within the cutout of the knife carrier to obstruct advancement of the knife carrier to a second position in which the engagement portion is spaced from the central bore of the inner housing portion of the shell housing and the locking tang is removed from the cutout of the knife carrier.

9. The circular stapling device of claim 8, wherein the inner housing portion of the shell assembly includes a bushing, and the spring clip is supported about the bushing.

10. The circular stapling device of claim 9, wherein the bushing defines a recess that extends at least partially about the bushing and the spring clip is supported within the recess.

11. The circular stapling device of claim 10, wherein the bushing includes spaced flanges that define the recess, the locking tang of the spring clip extending radially outwardly of the flanges when the spring clip is in the first position.

12. The circular stapling device of claim 9, wherein the bushing defines a slot that communicates the recess with the central bore of the inner housing portion of the shell housing, the engagement portion of the spring clip extending across the slot into the central bore when the spring clip is in the first position.

13. The circular stapling device of claim 8, wherein the trocar is movable between the advanced and retracted positions through the central bore of the inner housing portion.

14. The circular stapling device of claim 13, wherein the anvil shaft is positioned to engage the engagement portion of the spring clip to move the spring clip from its first position to its second position when the anvil assembly is moved towards the clamped position.

15. The circular stapling device of claim 13, wherein the trocar is positioned and configured to engage the engagement portion of the spring clip to move the spring clip from its first position to its second position when the anvil assembly is moved towards the clamped position.

16. The circular stapling device of claim 8, wherein the pusher includes an annular pusher and a pushing member, the pushing member including fingers that are received within the staple pockets of the staple cartridge.

17. The circular stapling device of claim 8, further including a handle assembly, the elongate body being supported on the handle assembly.

18. The circular stapling device of claim 8, wherein the elongate body is adapted to be coupled to a robotic surgical system.

* * * * *